April 5, 1932. L. BURBANK Plant Pat. 12
PLUM
Filed Sept. 23, 1930
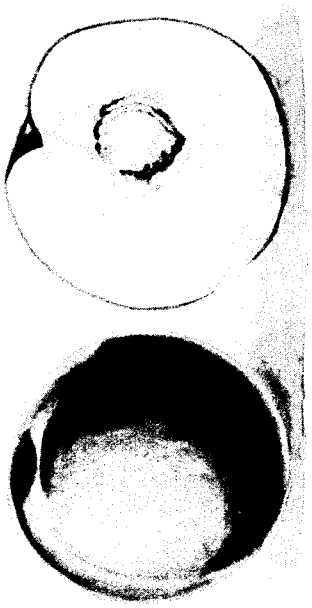
E. W. BURBANK
Executrix of
LUTHER BURBANK, Deceased
By Robb & Robb
Attorneys Patented Apr. 5, 1932

Plant Pat. 12

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S. NURSERIES & ORCHARDS COMPANY, OF LOUISIANA, MISSOURI

PLUM

Application filed September 23, 1930. Serial No. 483,934.

This invention relates to a new and distinct variety of plum.

This new variety is a distinctively different and better early, red, freestone plum, embodying only the desired qualities that combine and result in a plum which ripens extremely early. It is of great size and a freestone with small seed, a heavy bearer and exceptionally hardy. This plum has every good characteristic that a desirable plum should have in size, shape, beauty and stability under shipping conditions.

The annexed drawings and following specification manifest the outstanding distinctions and characteristics of the new variety which has been asexually reproduced.

*Young trees in nursery row*

*Tree.*—The young trees in the nursery row are of vigorous growth, with strong, well knit, acute forks. The older bark is dark brown with heavy gray scarfskin which is roughened by irregular cracks. This cracked bark discloses a yellow-brown under bark. The lenticels are numerous and of buff color, transversely elongated and very distinct during the second year's growth.

*Twigs.*—The twigs are slender with short internodes. The bark of the twigs is smooth and slightly glossy. The older portions show an apple green undercolor, shading to biscay green. The upper or exposed surface is shaded verona brown to terracotta, and ochre red on the younger twigs. The dormant buds are very small, quite blunt, free and dark brown in color. (The above colors are in accordance with Ridgeway's color standard.)

*Foliage.*—The leaf is small, being about 2½ inches long and 1⅜ inches wide, with an ovate form inclined to obovate; has an acute base, the apex of which tapers to almost acuminate. The texture is thick and brittle with an especially harsh undersurface because of the prominent protruding veins. The margin is regular, double crenate, usually glandular tipped. The upper surface is uneven, and of a slightly glossy forest green in color. The under or lower surface is modified to light bice green by a surface layer of white cells. There is a noticeable brownish pubescence on the midrib and at the base of the veins. Both the ribs and the veins are stiff and prominent giving harshness to the general appearance.

*Petiole.*—The petioles are rather slender, being from ⅜ to ½ inch in length, and are grooved on the upper side. The color continues the ochre red of the twigs with a tinge of red extending to the midrib. There are usually two rather large glands, flattened globose or almost cupped which are brownish in color.

*Full grown trees*

*Tree.*—The tree's growth is moderate, rather dense with upright to spreading branching habit. The branches are stiff and strong; forks acute, angle about 30 degrees from vertical. The older bark is rough, resembling that of the Prunus hortulana species. The cracks are irregular with cross checking of the bark resulting in exfoliation of more or less rectangular flakes, giving the trunk an exceedingly rough appearance.

*Foliage.*—The mature leaves are rather small to a medium size and shaped oval to slightly ovate, being 2¾ to 3 inches long and 1⅝ to 2 inches wide. The texture is moderately rough and is quite stiff. The upper surface is rather harsh in appearance, rugose with midrib and veins depressed. The color is dark green being modified by slight pubescence. The under surface is similar to the upper surface in color though the general effect is modified by the whitish veins, the midrib being darkened by a heavy brownish pubescence. The base is broadly acute to rounded. The margin is irregularly crenate; apex often narrowly acute, usually twisted.

*Petiole.*—The petiole is moderately stout, pubescent; strongly tinged purplish red and are from ⅜ to ½ inch in length. The glands are variable, often absent, but there are usually two if developed, being large and round, dark brown in color and located at or near the base of the blade.

*Twigs.*—The twigs are slender, the new growth being green tinged with brown. Internodes are short; leaf scars rather small.

The leaf and fruit buds are small and about the same size. The twigs are swollen just below the buds.

*Fruit*

*Form.*—The shape of the plum is globular inclined to oval with unequal sides. The sizes is medium to large, having about a 2 inch axial diameter and 1⅞ inches transverse diameter. The cavity is small, narrow and abrupt. The suture is broad but shallow yet distinctly marked as a yellowish line or stripe. The apex is round or slightly flattened.

*Color.*—The surface is glossy, being in color a dull deep crimson shading to purple. The surface has numerous conspicuous dots, russet in color, modifying both surface and color, giving the plum quite a characteristic appearance.

*Skin.*—The skin is fairly thick and tough, somewhat acidulous or tart, and clings to the flesh.

*Stone.*—The stone or seed is round, small for size of fruit (about $\frac{11}{16}$ inch long and $\frac{9}{16}$ inch wide and $\frac{5}{16}$ inch thick). The ventral suture is a sharp winged ridge with a distinct groove on each side extending from stem end to apex. The dorsal suture is a deep groove with irregular notched edges. Apex is mucronate. Sides of stone are minutely pitted, with sharp ridges near stem end. Color is clear light buff. The seed is free.

*Flesh.*—The flesh is firm and solid, slightly fibrous and fine grained, is moderately juicy with a mild flavor. The flesh color is a light golden yellow.

Although herein are stated the general characteristics of the plum, it is understood they may vary slightly due to soil or climatic conditions.

What is claimed is:

The plum tree herein described, characterized by the ripening period of its fruit and the freestone characteristic of its seed, as shown.

In testimony whereof I affix my signature.

ELIZABETH WATERS BURBANK,
*Known also as Elizabeth Burbank, Executrix of Luther Burbank, Deceased.*